United States Patent
Pegan et al.

(10) Patent No.: US 10,161,737 B2
(45) Date of Patent: Dec. 25, 2018

(54) FLEXIBLE SENSOR APPARATUS

(71) Applicant: The Regents of the University of California, Oakland, CA (US)

(72) Inventors: Jonathan Pegan, Irvine, CA (US); Michelle Khine, Irvine, CA (US); Mark Bachman, Irvine, CA (US); Joshua Kim, Oakland, CA (US); Sun-Jun Park, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/311,990

(22) PCT Filed: May 18, 2015

(86) PCT No.: PCT/US2015/031438
§ 371 (c)(1),
(2) Date: Nov. 17, 2016

(87) PCT Pub. No.: WO2015/179320
PCT Pub. Date: Nov. 26, 2015

(65) Prior Publication Data
US 2017/0219331 A1    Aug. 3, 2017

Related U.S. Application Data

(60) Provisional application No. 62/000,458, filed on May 19, 2014, provisional application No. 62/088,486, (Continued)

(51) Int. Cl.
*G01L 13/06* (2006.01)
*G01B 7/16* (2006.01)
(Continued)

(52) U.S. Cl.
CPC ............ *G01B 7/20* (2013.01); *A61B 5/113* (2013.01); *G01L 1/2287* (2013.01);
(Continued)

(58) Field of Classification Search
CPC ... G01B 7/20; A61B 5/113; A61B 2562/0261; A61B 2562/164
(Continued)

(56) References Cited

U.S. PATENT DOCUMENTS

| 2005/0080349 | A1 | 4/2005 | Okada et al. | |
| 2006/0169989 | A1* | 8/2006 | Bhattacharya | H01L 51/0021 257/79 |

(Continued)

FOREIGN PATENT DOCUMENTS

CN 103219066 A 7/2013

*Primary Examiner* — Max Noori
(74) *Attorney, Agent, or Firm* — Knobbe, Martens, Olson & Bear, LLP

(57) ABSTRACT

A sensor apparatus including a flexible substrate and a wrinkled conductor disposed on the flexible substrate. In some embodiments, the conductor includes micro-scale invaginations. Also disclosed are methods of making a sensor apparatus, including: placing a mask over a polymeric sheet, wherein the mask is configured to block regions of the polymeric sheet, depositing a conductive structure on the polymeric sheet at regions exposed through the mask, shrinking the polymeric sheet with conductive structure patterned on its surface by heating, and transferring the conductive structure to a flexible substrate. Also disclosed are methods of sensing a health condition of a user or patient. The methods include coupling a sensor apparatus to a surface of a user or patient overlying structures to be monitored. The sensor apparatus may include a crumpled conductor capable of detecting strain. Strain is detected by directing current through the sensor apparatus during flexing of the surface and measuring a characteristic of the sensor (Continued)

apparatus based on the strain to generate an output for a user, indicative of the condition of the user or patient.

20 Claims, 13 Drawing Sheets

Related U.S. Application Data filed on Dec. 5, 2014, provisional application No. 62/147,979, filed on Apr. 15, 2015.

(51) Int. Cl.
*G01L 1/22* (2006.01)
*A61B 5/113* (2006.01)

(52) U.S. Cl.
CPC ............... *A61B 2562/0261* (2013.01); *A61B 2562/0285* (2013.01); *A61B 2562/164* (2013.01)

(58) Field of Classification Search
USPC .............................................. 72/774; 73/774
See application file for complete search history.

(56) References Cited

U.S. PATENT DOCUMENTS

| | | | |
|---|---|---|---|
| 2006/0283262 A1* | 12/2006 | Smits | G01N 27/041 73/799 |
| 2011/0278040 A1 | 11/2011 | Zhang et al. | |
| 2012/0086433 A1 | 4/2012 | Cheng et al. | |
| 2012/0121870 A1 | 5/2012 | Toury et al. | |
| 2013/0140611 A1* | 6/2013 | Kim | H01L 29/84 257/254 |
| 2013/0264912 A1* | 10/2013 | Kwon | C09D 127/16 310/365 |
| 2014/0054599 A1* | 2/2014 | Choi | H01L 31/03044 257/76 |
| 2015/0034237 A1* | 2/2015 | Biggs | H01L 41/047 156/234 |
| 2015/0263235 A1* | 9/2015 | Shin | H01L 33/38 257/72 |
| 2015/0294805 A1* | 10/2015 | Hayward | C23C 14/042 200/511 |

\* cited by examiner

*Before Shrinking*

*After Shrinking*

FLEXIBLE SENSOR APPARATUS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field

This application is directed to sensors that can withstand high degrees of strain while still producing useful outputs. In specific examples, thin strain gauges are disclosed that can undergo high strain while providing repeatable, predictable changes in resistance to be able to measure strain or loads.

Description of the Related Art

Strain gauges are known, including thin film strain gauges. These devices are useful over small ranges of strain. For example, conventional metal foil strain gauges function well at or below 5% strain.

SUMMARY OF THE INVENTION

Various applications would benefit from strain gauges that can undergo large strains and still produce repeatable, predictable outputs. For example, it is desired that such a strain gauge or other sensor apparatuses can be mounted on a flexible substrate and connected to surfaces that are highly curved, mobile and/or repeatedly flexed during the duty cycle of the strain gauge or sensor apparatus. It would be useful for a sensor apparatus herein to be wearable to enable various health or physiological condition monitoring applications.

Some embodiments relate to a sensor apparatus comprising:
a flexible substrate, and
a conductor disposed on the flexible substrate, wherein the conductor is capable of repeatable variation in resistance when subject to a strain of up to about 900%.

In some embodiments, the conductor is capable of repeatable variation in resistance when subject to a strain of up to about 330%.

In some embodiments, the conductor is capable of repeatable variation in resistance when subject to a strain of up to about 300%.

In some embodiments, the conductor is capable of repeatable variation in resistance when subject to a strain of up to about 150%.

In some embodiments, the conductor is capable of repeatable variation in resistance when subject to a strain of more than 5%, 10%, 15%, 20%, 30%, 40%, 50%, 60%, 70%, 80%, 90%, 100%, 110%, 120%, 130%, 140%, 150%, 160%, 170%, 180%, 190%, 200%, 250%, 300%, 350%, 400%, 450%, 500%, 550%, 600%, 650%, 700%, 750%, 800%, 850%, up to about 900%.

In some embodiments, the conductor comprises secondary folding.

In some embodiments, the secondary folding comprises micron-scaled invaginations in the surface of the conductor.

In some embodiments, the conductor is a metal film.

In some embodiments, the conductor comprises any material suitable for processes conventionally used for semiconductor fabrication, e.g., sputtering or deposition, or comprise a material or configuration selected from the group consisting of a semiconductor structure, carbon nanotubes and carbon black.

In some embodiments, the metal film comprises a gold layer.

In some embodiments, the metal film comprises a platinum layer.

In some embodiments, the flexible substrate comprises an elastomeric polymer.

In some embodiments, the elastomeric polymer is an elastomeric silicone film.

In some embodiments, the elastomeric silicone film comprises polydimethylsiloxane.

In some embodiments, the elastomeric polymer is ECOFLEX™ from Smooth-on, Inc., which uses a platinum curing agent. ECOFLEX™ is softer than PDMS, and correspondingly more stretchable.

Some embodiments relate to a strain gauge, comprising:
a flexible substrate, and
a conductor deposited on the flexible substrate, wherein the conductor comprises micron-scale invaginations.

In some embodiments, the micron-scale invaginations comprise a heterogeneous structure.

In some embodiments, the flexible substrate is configured to be mounted to the skin of a user or patient.

Some embodiments relate to a method of making a sensor apparatus, comprising:
placing a polymeric sheet between a support and a mask configured to block regions of the polymeric sheet,
depositing a conductive structure on the polymeric sheet at regions exposed through the mask,
shrinking the polymeric sheet with conductive structure patterned on its surface by heating, and
transferring the conductive structure to a flexible substrate.

In some methods, the flexible substrate is an elastomeric polymer.

In some embodiments, the method further comprising casting the flexible substrate on the same surface of the polymeric sheet where the conductive structure is deposited.

In some methods, the polymeric sheet comprises a shape-memory (shrink-wrap) polyolefin (PO) film.

In some methods, the polymeric sheet comprises polystyrene.

Some embodiments relate to a method of sensing a health condition of a user or patient, comprising:
coupling a sensor apparatus to a surface of a user or patient overlying structures to be monitored, the sensor apparatus including a crumpled conductor capable of detecting strain;
directing current through the sensor apparatus during flexing of the surface; and
measuring a characteristic of the sensor apparatus based on the strain to generate an output for a user indicative of the condition of the structures to be monitored.

In some embodiments, the characteristic of the sensor is a change in the resistance of a conductor thereof.

In some embodiments, movement of the surface is in response to breathing of the patient or user and the output indicates respiration of the user or patient.

In some embodiments, movement of the surface is in response to motion of the underlying structure, e.g., diaphragm or internal organs.

Also disclosed is a process to densify and align one dimension nanostructuress, such as carbon nanotubes (CNTs) or silicon nanowires (SiNWs), comprising depositing a thin film of a one dimension nanostructures, such as CNTs or SiNWs on the surface of a shape memory polymer and shrinking the thin film of CNTs or SiNWs in at least one direction.

In some embodiments, the process further comprises uniaxially shrinking the thin film.

In some embodiments, the process further comprises biaxially shrinking the thin film.

In some embodiments, the shape memory polymer is a chemically resistant shape memory polymer.

In some embodiments, the shape memory polymer is a polyolefin.

In some embodiments, the CNTs or the Si NWs deposited on the surface of the shape memory polymer is dispersed in a solution of an organic solvent.

In some embodiments, the organic solvent is chloroform.

In some embodiments, the shape memory polymer is placed on the surface of an aqueous solution during said depositing a thin film of CNTs or SiNWs on the surface of a shape memory polymer.

In some embodiments, the uniaxially, biaxially, or multiaxially shrinking the thin film of CNTs or the thin film of SiNWs can be done by heating.

In some embodiments, the heating is done at a temperature of from 50-250° C.

In some embodiments, the heating is done at a temperature of 150° C.

In some embodiments, the thin film of CNTs or the thin film of SiNWs is deposited on the surface of the shape memory polymer with an airbrush.

Some embodiments relate to a film of highly dense and aligned carbon nanotubes prepared by the disclosed processes of densifying and aligning carbon nanotubes (CNTs) or silicon nanowires (SiNWs) comprising depositing a thin film of CNTs or a thin film of SiNWs on the surface of a shape memory polymer and shrinking the thin film of CNTs or the thin film of SiNWs in at least one direction.

In some embodiments of film, the density of CNTs or SiNWs results in a light transmittance value of about 40%.

In some embodiments of film, the electrical resistance of the film is about 300 kΩ.

Some embodiments relate to a method, comprising: forming a film of carbon nanotubes (CNTs) or silicon nanowires (SiNWs) on a substrate, the nanotubes having an average separation in a direction transverse to longitudinal axes thereof; and reducing the average separation of the nanotubes by shrinking the substrate in one direction.

Some embodiments relate to a method of forming a wrinkled CNT film or a wrinkled SiNW film, comprising: forming a film of carbon nanotubes (CNTs) or a thin film of silicon nanowires SiNWs on a substrate; and reducing the average separation of the nanotubes by biaxially or multi-axially shrinking the substrate, thereby forming the wrinkled CNT film or the wrinkled SiNW film.

Some embodiments relate to methods of sensing a health condition of a user or patient. The methods include coupling a sensor apparatus to a surface of a user or patient overlying structures to be monitored. The sensor apparatus may include a crumpled conductor capable of detecting strain. Strain is detected by directing current through the sensor apparatus during flexing of the surface and measuring a characteristic of the sensor apparatus based on the strain to generate an output for a user, indicative of the condition of the user or patient.

BRIEF DESCRIPTION OF THE DRAWINGS

FIG. 11. SEM images of wrinkled CNT thin film at various magnifications. (A) 3,250× magnification; (B) 17,500× magnification; and (C) 4,000× magnification.

DETAILED DESCRIPTION OF THE PREFERRED EMBODIMENT

Disclosed herein is a sensor apparatus, e.g., a strain gauge or sensor, including a flexible miniaturized sensor. The physical structure of the flexible miniaturized sensor enables it to exhibit predictable, repeatable changes in resistance to current flow over a much larger range of strain than had been known before.

A. Flexible Miniaturized Sensor Apparatuses

FIGS. 1-12 illustrate a variety of structures that can be incorporated into the sensor apparatus 100 to reliably detect a fluctuating signal, such as a detectable change in resistance, for motion detection in a disposable wearable sensor. FIGS. 1-8 illustrate thin film metal strain gauges, FIGS. 9-12 illustrate one-dimensional structures, including nanotubes and nanowires for use as disposable wearable strain gauge sensors.

1. Sensors Having a Metal Film Conductor

Figure 1:
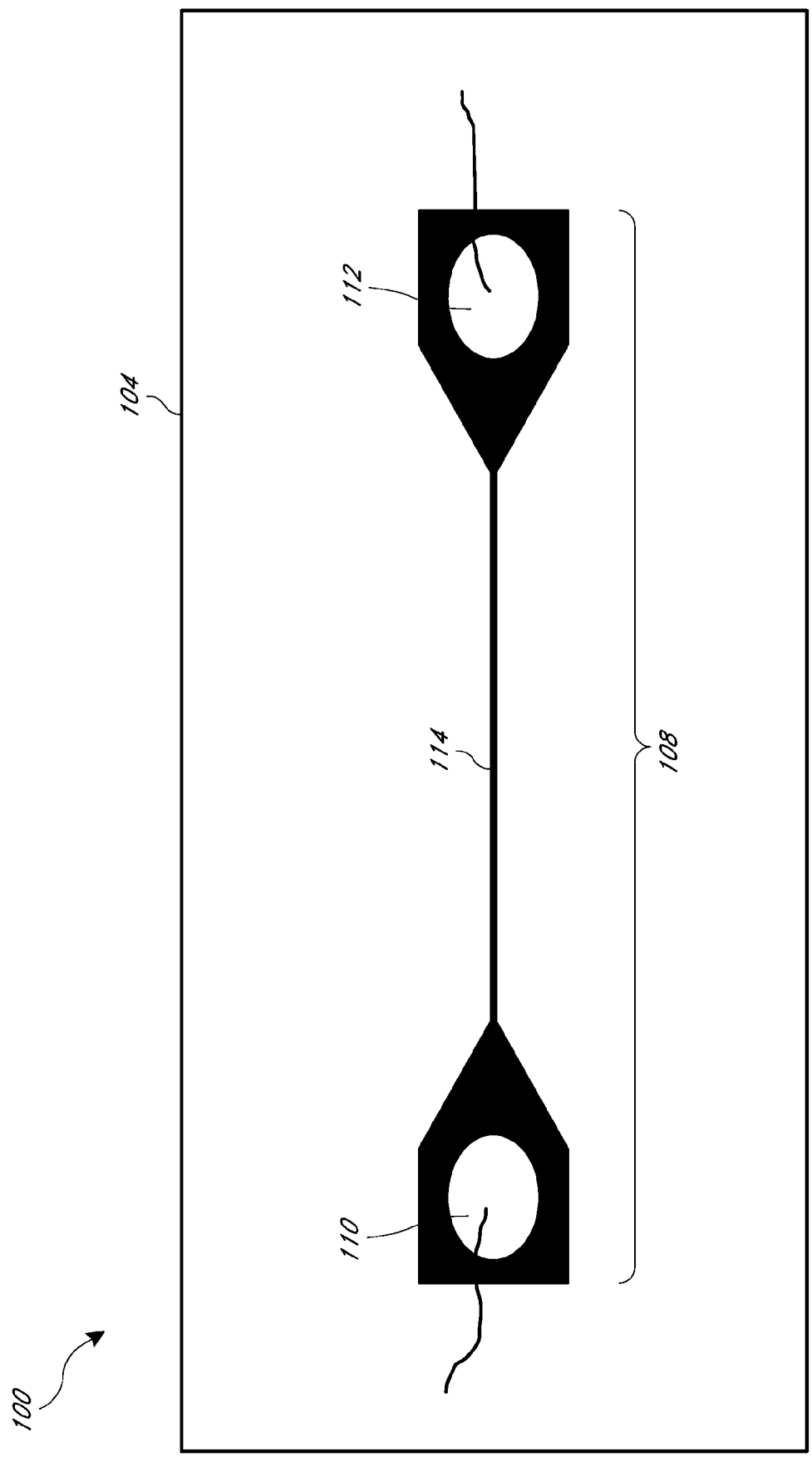
FIG. 1 depicts a wrinkled metal film strain gauge.
Figure 2:
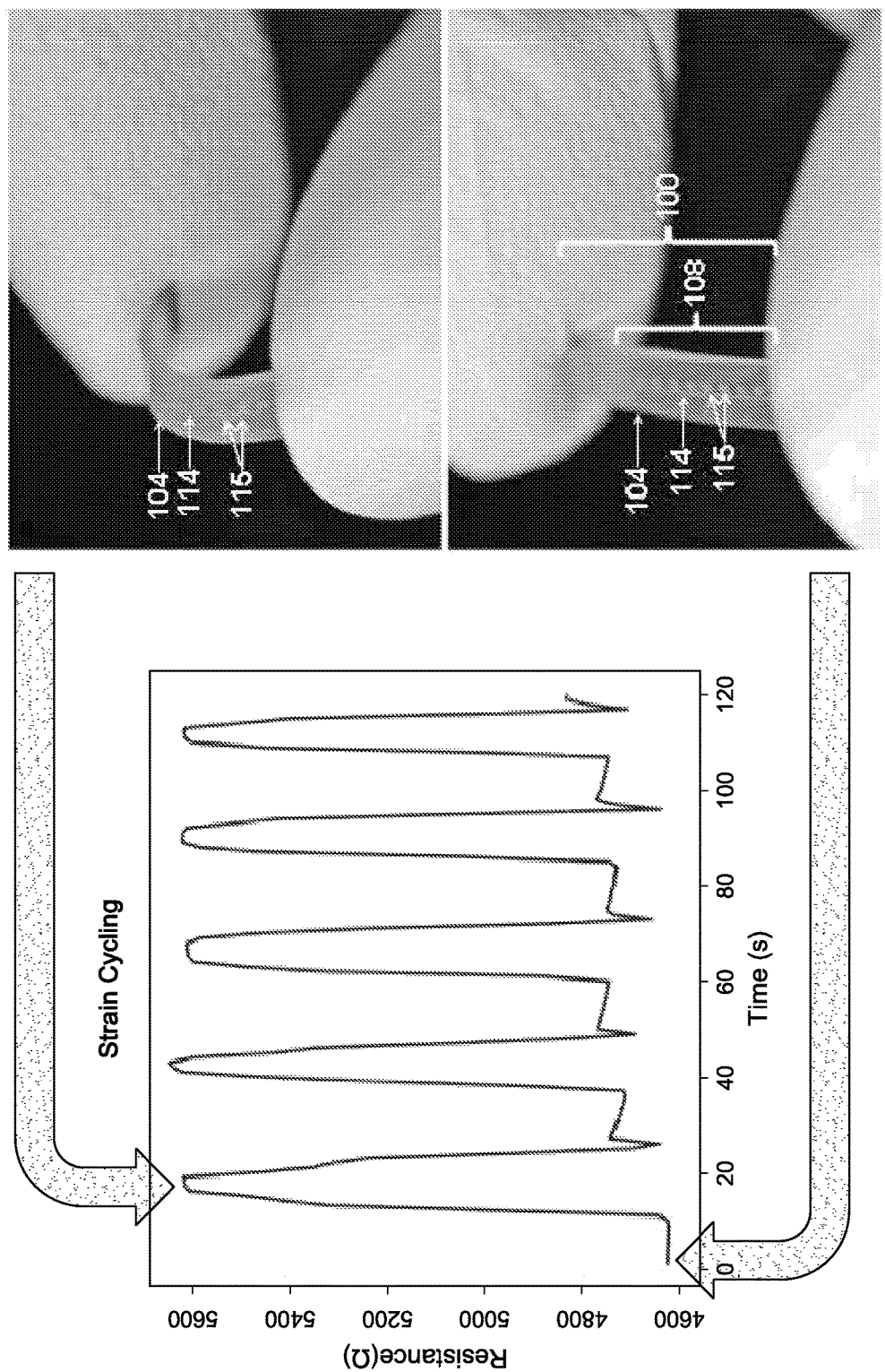
FIG. 2 shows the resistance response of a wrinkled metal film strain gauge. Resistance peaks correspond with maximum strain of 5%. The bottom arrow indicates the initial, unstrained resistance of the wrinkled metal film strain gauge.

In one embodiment, as depicted in FIG. 1, the sensor apparatus 100 includes a flexible substrate 104 and a conductor 108. In the illustrated embodiment, the conductor 108 initially is formed as a thin metal film but thereafter crumpled or wrinkled because the material it is formed upon is shrunk to a fraction of its initial size. A plurality of electrical contacts 110 and 112 are in electrical communication with the conductor 108. The electrical contacts 110, 112 can be disposed at opposite ends of an elongate conductive region 114. In other embodiment, more than two contacts can be provided. For example, FIG. 2 shows one modified embodiment in which a plurality of contacts 115 are disposed along the length of an elongate conductive region 114 on flexible substrate 104. The contacts 115 in this embodiment are disposed to one side of the elongate conductive region and allow connection to other devices at a number of different positions and/or permit a number of different devices to be in contact with the elongate conductive region. For example, any two of the contacts 115 can be used to measure a signal such as current or a change in a property such as resistance at a location along the conductive region 114.

The sensor apparatus 100 is able to undergo very high strain, which induces a detectable change in a signal as illustrated in FIGS. 2 and 3. The signal can be a change in resistance.

Figure 3A:
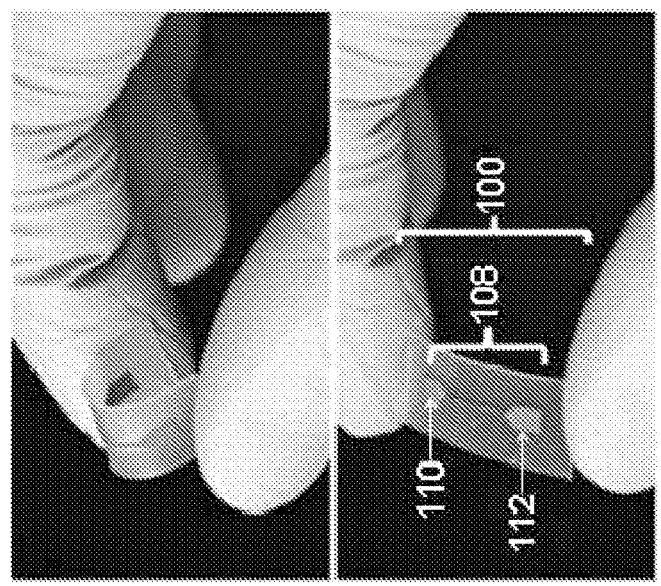
FIG. 3 shows strain cycling of a second embodiment of a wrinkled metal film strain gauge. Panels (A) and (B) show semi-static linear strain cycling. Panel (C) is a top down scanning electron micrograph (SEM) of adjacent wrinkles in contact.
Figure 3A:
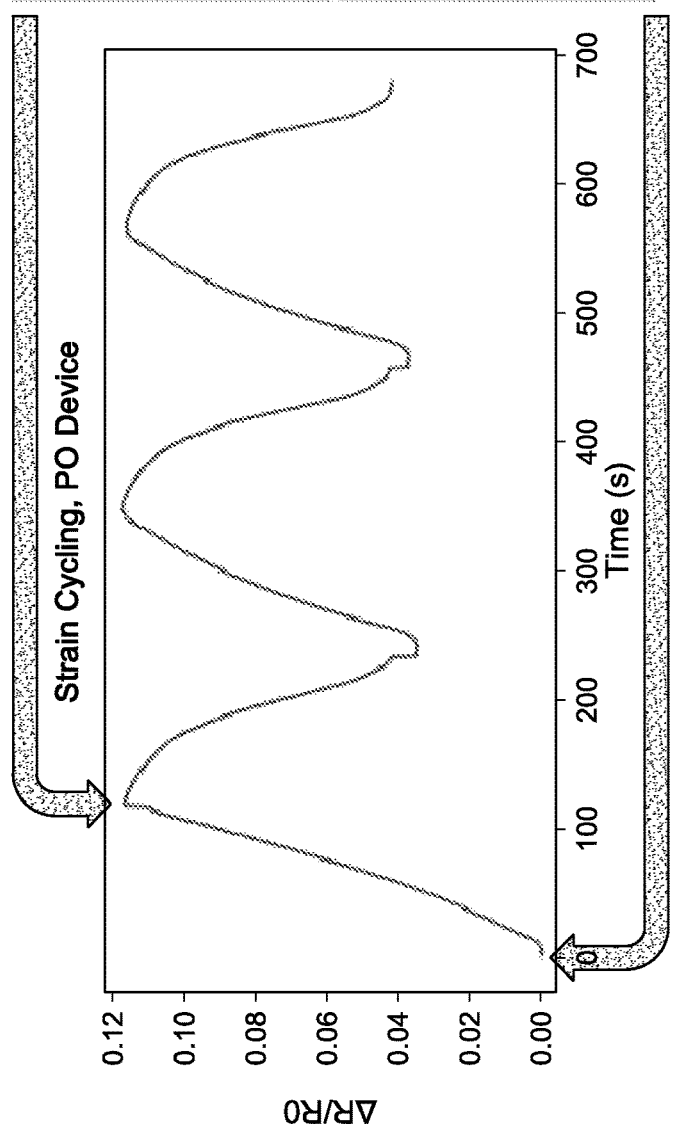
Figure 3B:
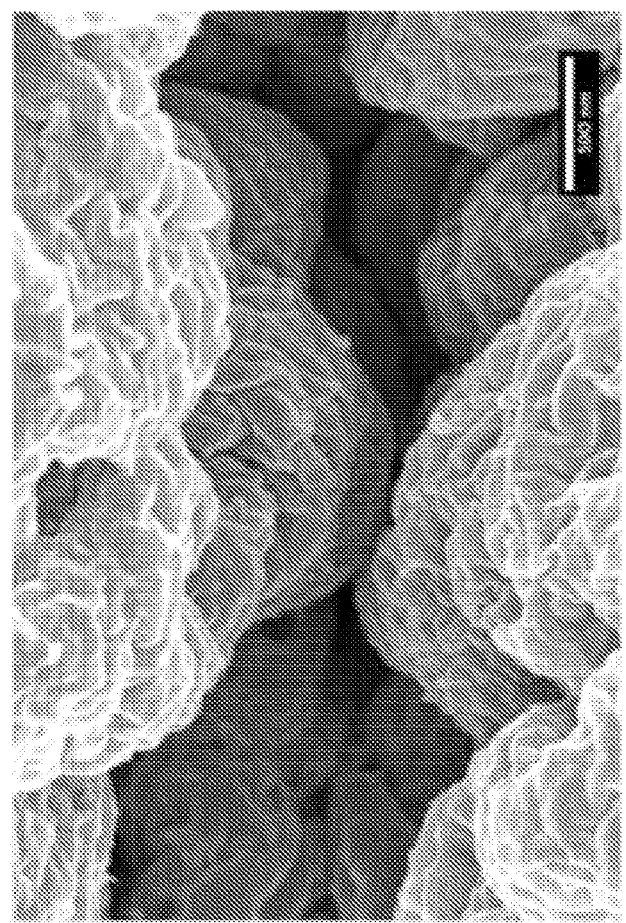
Figure 3C:
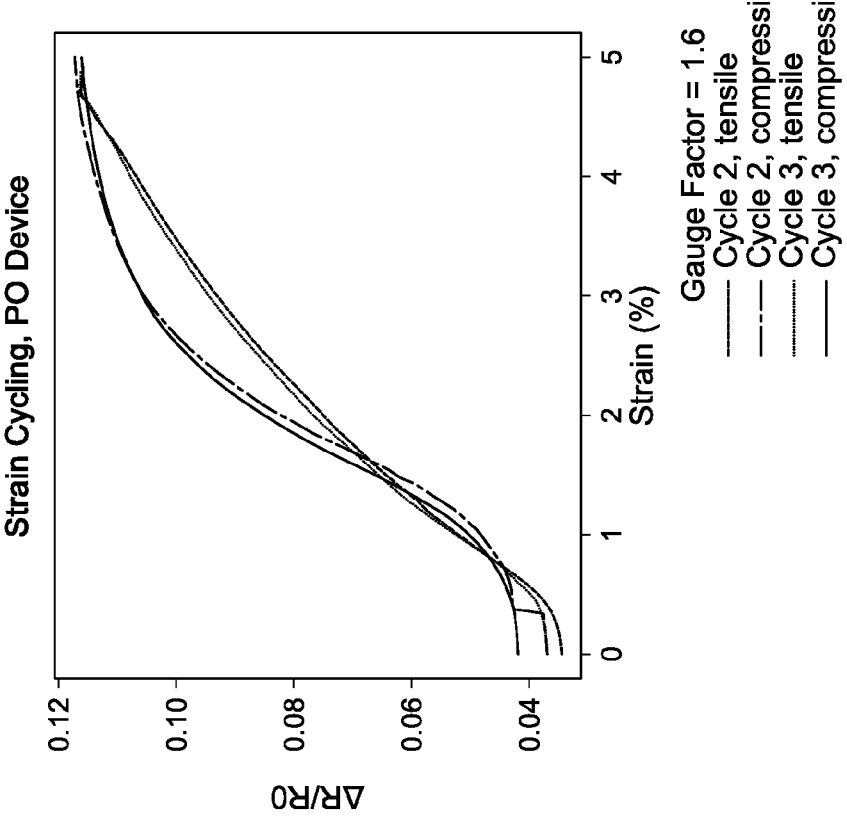

One configuration that enables high range of strain is the physical configuration of the film conductor 108. In particular, as shown in FIG. 3(C), at the micron-scale the conductor 108 is not flat but rather is crumpled or wrinkled. This configuration can exhibit secondary folding in some embodiments. Non-shrunk and shrunk electrodes have a linear decrease in resistance across patterned line electrodes of different widths. Measuring electrical resistivity before and after the thermal shrinking process shows a dramatic improvement in electrical conductivity of wrinkled Au thin film electrodes over the non-shrunk, planar Au electrodes. Cross-sections of the wrinkled metal films reveal many tens of micron-scale invaginations in the surface where adjacent wrinkles pack closely enough that they begin to coalesce, referred to as secondary folding. In a flat metal thin film, discontinuities produce a large effect in the resistivity of the film. Without wishing to be bound to any particular theory, we hypothesize that secondary folding in a wrinkled Au thin films creates an increase in electrical contacts, thereby circumventing these discontinuities and reducing the effective resistivity of the wrinkled thin film electrodes.

Moreover, the crumpled configuration of the conductor 108 allows for a great degree of extensibility when subject to strain. The conductor 108 is folded upon itself in the at-rest state and unfolds or unfurls when under strain to an elongate state without being subject to fracture. This mechanical integrity allows the conductor 108 to continue to function even when under strains that are severe for conventional thin film strain gauges.

a. Method of Forming High Strain Film Conductor

Figure 4:
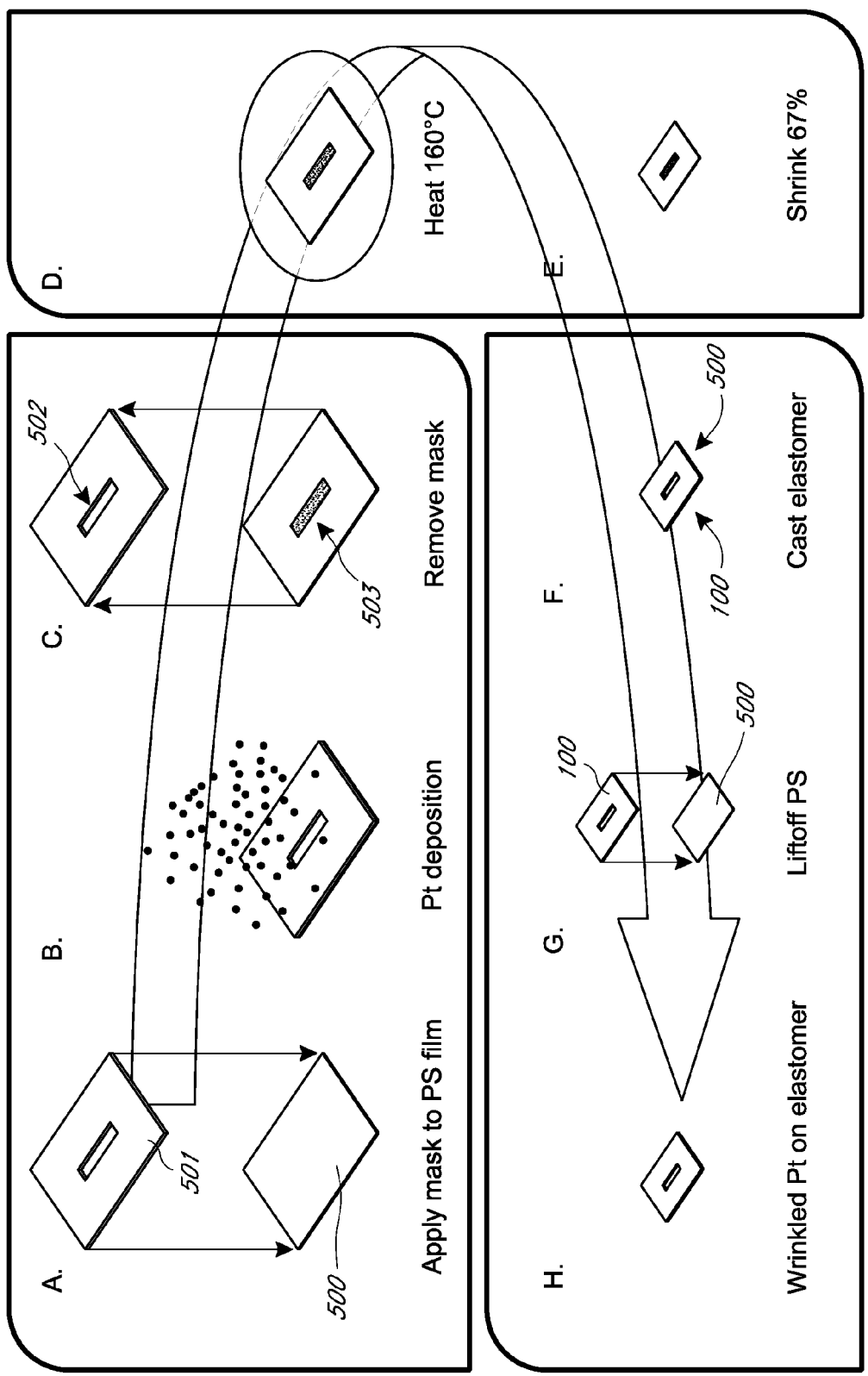
FIG. 4 illustrates a process for making and transferring a wrinkled metal thin film to an elastic material. The process can be separated into 3 sub-processes: Lithography (A-C), Miniaturization (D, E), and Transfer (F-H).

The micron-scale configuration discussed above can be provided by any suitable method. FIG. 4 shows one technique that involves exploiting a heat-shrink material. In FIG. 4, panel (A) the polystyrene shrink film is masked. In panel (B) a metal thin film is deposited. In panel (C), the mask is removed and in panels (D and E) the shrink film is heated to 160° C., shrinking the metal patterned polymer by about 67% by surface area. In panel (F), a flexible polymer, such as ECOFLEX 30™, is spin coated onto the shrunken sample and cured. In panel (G), a series of solvent baths or other separation technique is used to lift off the polystyrene, resulting in the wrinkled metal thin film transferred onto the silicon elastomer (panel H). In some embodiments, a polymeric sheet 500 of suitable heat-shrink characteristics is placed adjacent to a mask 501 configured to block regions of the polymeric sheet 500. This may be followed by a step of depositing a conductive structure 503 on the polymeric sheet 500 at regions exposed through the mask 502. After the conductive structure 503 is formed, the mask 501 can be removed. The process then follows with shrinking the polymeric sheet 500 with the conductive structure 503 patterned on its surface by heating. The metal-patterned polymer may be reduced in size with regard to surface area by 5%, 10%, 15%, 20%, 25%, 30%, 35%, 40%, 45%, 50%, 55%, 60%, 65%, 70%, 75%, 80%, 85%, 90% or 95%. Thereafter, the conductive structure 503 is transferred to a flexible substrate.

The conductive structure 503 can be deposited by any method, for example by air brushing or by electrospray of a material onto a surface. In some embodiments, the conductive structure 503 comprises any conductive metal. In some embodiments, the metal conductive structure is a thin metal film. In some embodiments the metal is selected from the group consisting of Cu, Ag, Au, and Pt. In some embodiments, the polymeric sheet 500 may be a shape-memory (e.g., a shrink-wrap) polyolefin (PO) film. The shrinking step may performed at a temperature of about 100° C., 110° C., 120° C., 130° C., 140° C., 150° C., 160° C., 170° C., 180° C., 190° C. 200° C., 210° C. or 250° C. Among the materials that are well suited for heat-shrink processing is polystyrene.

b. Sensor Assembly Including a High Strain Film Conductor and Flexible Medium

The foregoing method forms a suitable conductive structure for a sensing apparatus. However, many heat shrink materials are more rigid than would be preferred for some applications. For example, it may be desirable to configure the sensing apparatus with as little shape-retaining characteristics as possible. It may be desired to permit the sensing apparatus to drape over a natural structure such as a joint or an expanse of skin. It may be desirable to couple this highly conformal sensing apparatus to a platform that will retain mechanical integrity during continuous use of an hour or more, up to two hours, or even a period of twenty-four hours or more. Thus, it may be desired to transfer the conductive structure to a flexible substrate. The flexible substrate can provide mechanical backing for the highly conformal sensing apparatus while allowing it to retain sufficient flexibility to reliably and repeatedly detect movement.

In one method, it is desired to transfer the conductive structure 503 to an elastomeric polymer. One technique involves cast molding an elastomeric polymer support 504 onto the same surface of a heat-shrunk polymeric sheet 500 upon which the conductive structure 503 is deposited (see FIG. 4, step F). The cast molding can involve preparing the elastomeric material in liquid form and dispensing it onto the surface upon which the conductive structure 503 is deposited. The liquid elastomeric polymer is permitted to solidify. Thereafter, the conductive structure 503 is sandwiched between an elastomeric layer of the support 504 and the heat-shrunk polymeric layer 500. Thereafter, the heat-shrunk polymeric layer 500 optionally is removed (see FIG. 4, step G), leaving the conductive structure 203 on the surface of the elastomeric layer of the support 504.

Metal patterns can be fabricated directly on polydimethylsiloxane (PDMS) by using stencil masks or photolithography; however, there are some limitations to these methods, such as being restricted to patterns with only simple structures, contamination by wet chemicals and cracks because of a large mismatch in the coefficient of thermal expansion of PDMS and that of metals. More importantly, after direct metal patterning on PDMS, high-temperature processes (e.g., annealing) cannot be applied to the sample because of the low melting point of PDMS. Instead of direct-metal patterning on PDMS, it has been reported that metal patterns can be prepared on rigid substrates (e.g., Si or glasswafer); and then the patterns can be transferred to receiver substrates (e.g., PDMS).

For flexible electronics, a strong bond between the metal and the PDMS substrate is very important in order to fabricate a robust and reliable device that is able to endure the stresses induced by the bending of the substrates. If the metal patterns do not bond strongly to the PDMS surface, they can be damaged or lifted off easily by the applied voltage or fluidic pressure. For example, evaporated Au does not adhere to PDMS due to the weak interaction to PDMS.

An adhesion layer is optionally placed between the conductive structure and the elastomeric layer. In some embodiments, Pt is deposited first on a polymeric material, such as polystyrene (see FIG. 4, step B). This may be followed by deposition of a thin layer of Au, which forms metallic bonds with the Pt. Any silane molecule may be used as a surface adhesion molecule. For example, when silicon (e.g., polydimethylsiloxane (PDMS)) is used as the elastomer, the thin film of Au can be covalently bonded to the silicon elastomer using 3-mercaptopropyl) trimethoxysilane (MPTMS) as a molecular adhesive (Byun I. et al. 2013 J Micromech Microeng 23(8): 1-10, incorporated herein by reference). Following heat-shrinkage of the polymeric material (see FIG. 4, steps D and E), the gold surface is treated with 3-mercaptopropyl) trimethoxysilane (MPTMS), which functions as a molecular adhesive in bonding the conductive layer to the silicon elastomer. When the wrinkled, conductive layer attached to the elastomer is lifted off of the heat-shrunk polymer, the Pt is exposed.

Several methods to promote adhesion between metal patterns and PDMS are known. The first is to use Ti or Cr as an adhesion interlayer and then activate and hydroxylate the respective surfaces of the metal and PDMS by oxygen plasma or UV/$O_3$ exposure in air. Conformal contact of two hydroxyl (—OH) groups on Ti (5 nm) surface (titanol) and hydroxylated PDMS surface (silanol) by oxygen plasma treatment results in permanent Ti—O—Si bonds. Cr (3 nm) and $SiO_2$ (30 nm) can be deposited on Au electrodes and delivered to PDMS, which is surface activated by exposure to UV/$O_3$, to form Si—O—Si linkages. Similarly, the adhesion can be enhanced between the metal electrodes and the PDMS by thermal curing a prepolymer of PDMS on Au electrodes with Ti interlayer (5 nm). However, using Cr or Ti as an adhesive layer can deteriorate the optical and electrochemical performance of the device, nor are these elements suitable for bio-applications. However, using a molecular adhesive that bonds to both the metal and PDMS may be an alternative to avoid the problems caused by additional metallic interlayers.

For a molecular adhesive, (3-mercaptopropyl) trimethoxysilane (MPTMS), as a self-assembled monolayer (SAM), is versatile because of the different functionality of its two terminal groups. Simultaneously, the three methoxy (—OCH$_3$) functional end groups can bind to oxide surfaces, while the thiol (—SH) functional head group can bind to metals. MPTMS has been used for the transfer of Au films to PDMS. Au patterns treated with MPTMS can bond to PDMS by pouring a PDMS prepolymer onto the Au patterns and subsequent thermal curing or bringing the Au patterns to PDMS whose surface was activated by exposure to UV/$O_3$. Not only Au, but also PDMS can be treated with MPTMS. This PDMS treated with MPTMS can bond with Au patterns by bringing them into contact.

Other alternative polymer elastomers may be used, such as urethane. For other types of polymer elastomers, corresponding adhesion methods are utilized.

The presence of an adhesion layer that adheres the conductive structure to the elastomeric substrate can significantly improve the dynamic range of a sensor. Without wishing to be bound to any particular theory, this may be because the conductive structure is anchored to the elastomeric substrate, allowing it to stretch in response to strain and to retract to its original conformation upon relaxation of the strain. In some embodiments, the dynamic range of a sensor containing an adhesion layer interposed between the conductive structure and the elastomeric layer is 10%, 20%, 30%, 40%, 50%, 60%, 70%, 80%, 90%, 100%, 110%, 120%, 130%, 140%, 150%, 160%, 170%, 180%, 190% or 100% greater than a comparable sensor that lacks an adhesion layer.

Further steps may involve encapsulating the conductive layer. Further steps may involve coupling the conductive layer with other devices, such as may be used to direct current through the conductive layer, to receive current directed through the conductive layer, to store and/or transmit data regarding the resistance or changes in resistance of the conductive layer, to provide one or more signals to the user or patient or for other purposes.

Figure 5A:
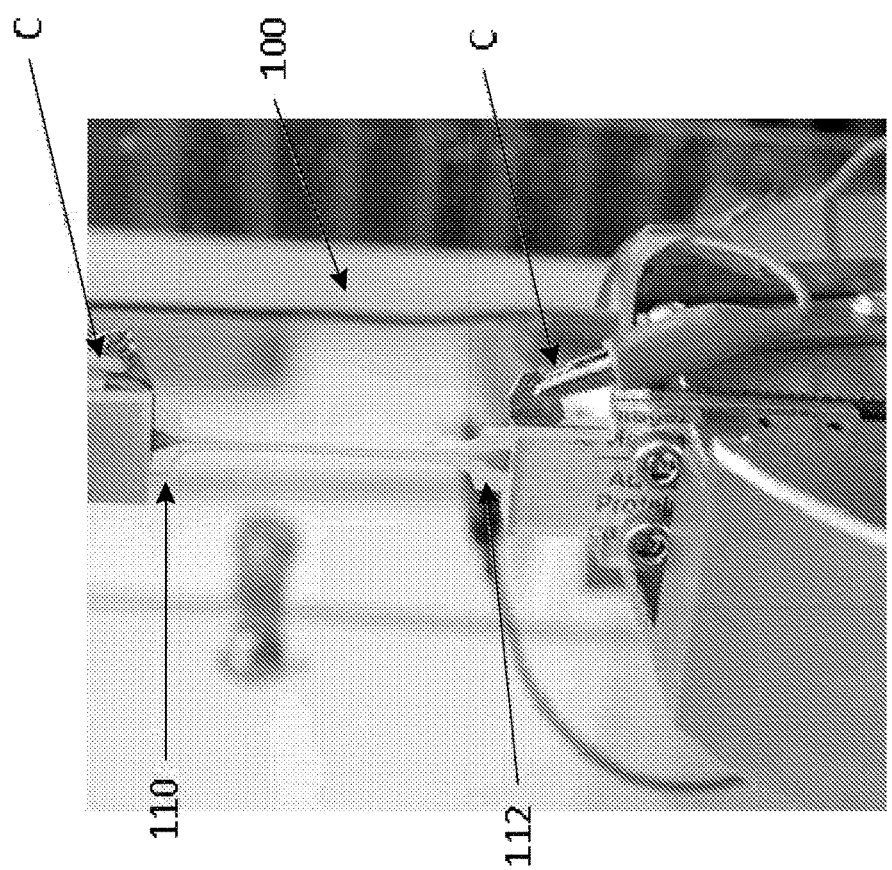
FIG. 5 (A and B) show mechanical integrity tests for an embodiment of a sensor apparatus.
Figure 5B:
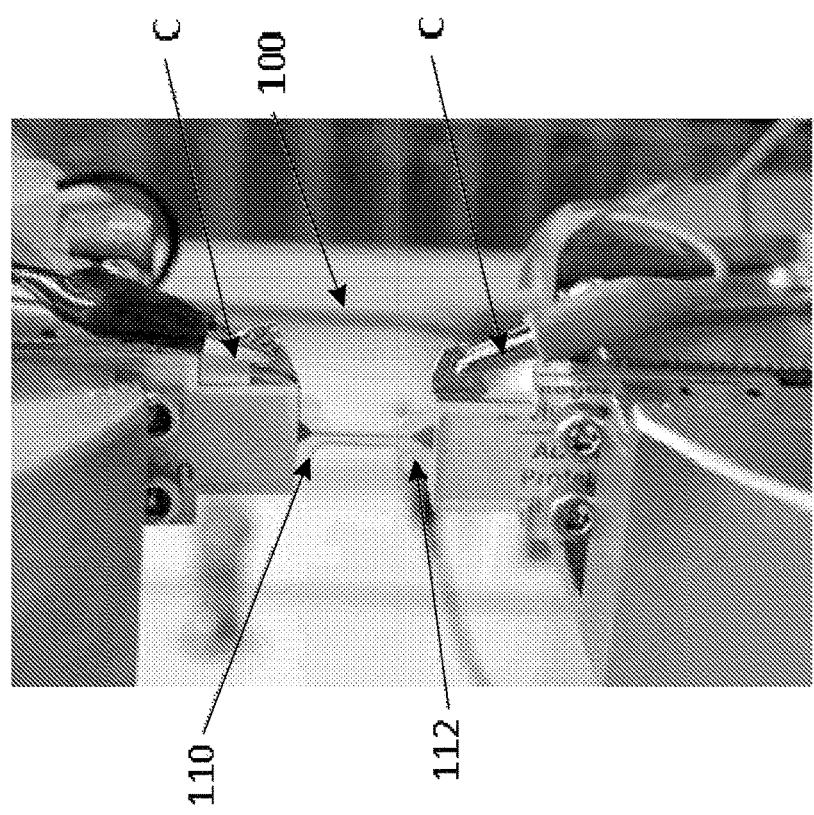

FIG. 5, A and B show mechanical integrity tests for an embodiment of the sensor apparatus 100. The sensor apparatus 200 includes the contacts 110, 112 which can be coupled with electrical conductors C as shown. The ends of the apparatus 100 are illustrated as being coupled with a pull test apparatus. The pull test apparatus pulls the ends of the apparatus 100 away from each other. In the test illustrated, current was caused to flow in a pulled state (panel B) through the sensor apparatus up to a strain of at least 150%. In at least one test a strain of 900% in a pulled state (panel B) was attained to show that the sensor apparatus 100 is able to stretch to a very high degree and still retain its overall structural integrity.

Figure 6A:
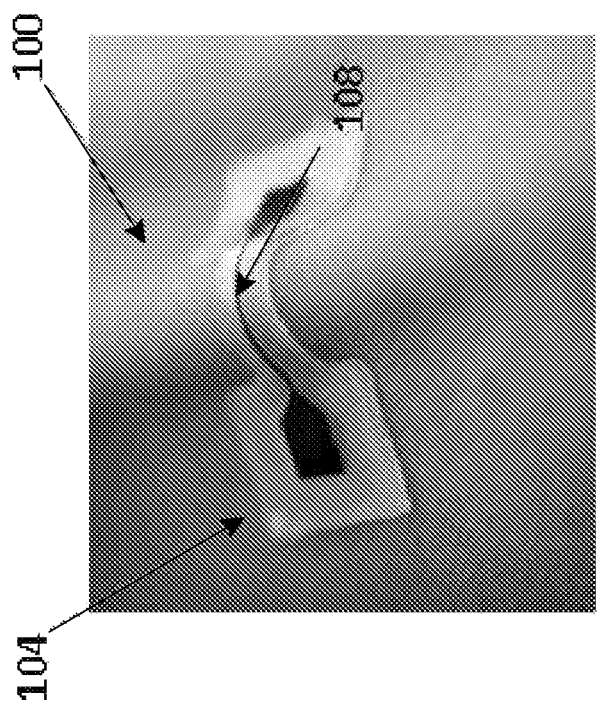
FIG. 6. (A and B) show conformability of an embodiment of a sensor apparatus according to the methods herein.
Figure 6B:
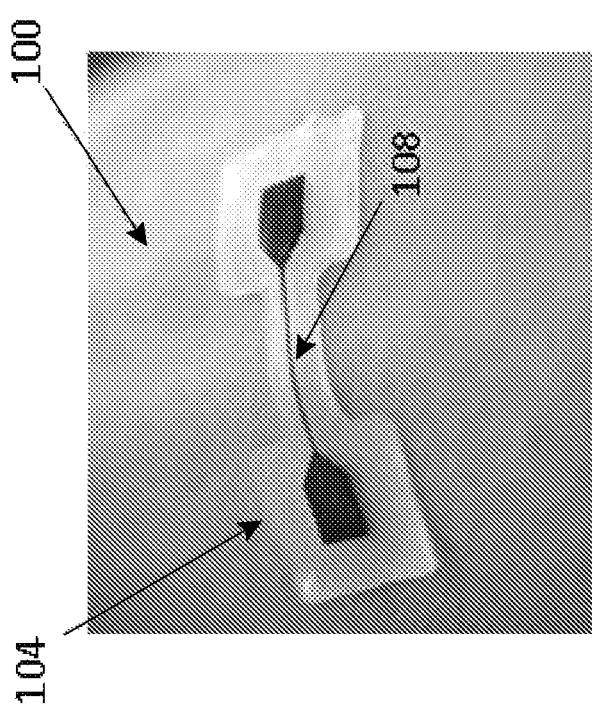

FIG. 6, A and B show gross mechanical characteristics of the sensor apparatus 100. The sensor apparatus 100 is very flexible and can be draped over a skin structure. The sensor apparatus 100 includes the thin film conductor 108, which is embedded in the flexible substrate 104. The flexible substrate 104 can at least partially encapsulate the thin film conductor 108. Panel A shows a rest state of the sensor apparatus 100 and the skin. Panel B shows a flexed state of the skin. That is, in this test the skin is gathered at a location spaced away from but close to the sensor apparatus 100. The gathering pulls the skin together, causing the ends of the apparatus 100 to move closer together. In this test, the ends move closer together with the skin. The sensor apparatus 100 is flexible so that the skin will return to the state of panel A after being moved to the position of panel B. The flexibility of the flexible substrate 104 is useful in that it helps to maintain the sensitivity of the thin film conductor 108 to the conditions to be sensed.

Figure 7A:
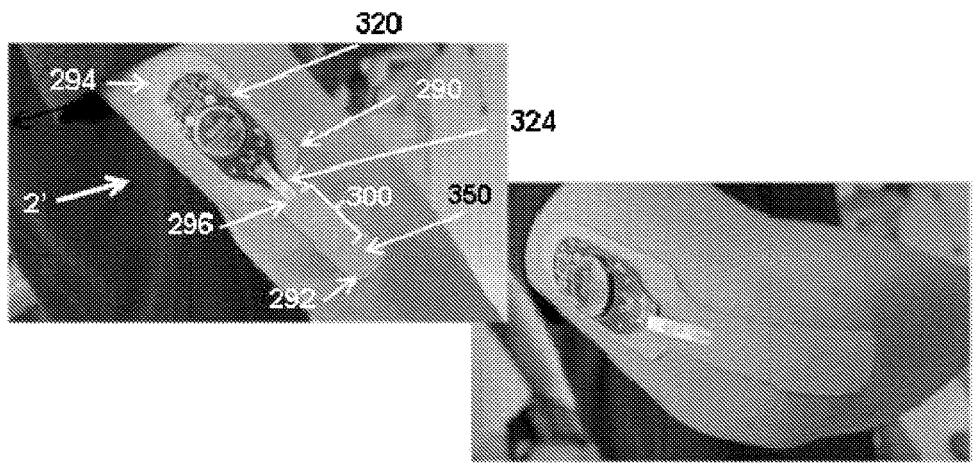
FIG. 7. (A) An assembly including a sensor apparatus and a sensor attachment module and shows an elbow flexion test that demonstrates the performance thereof. (B) Changes in resistance (ΔR/Ro) are measured as a function of elbow flexing.
Figure 7B:
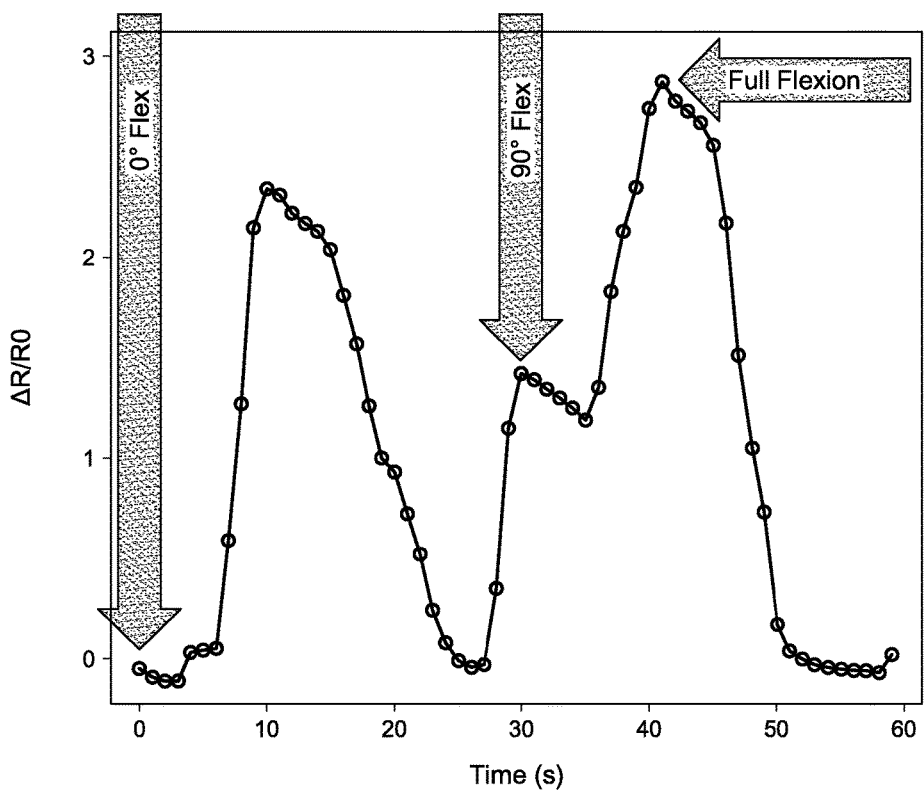
Figure 8A:
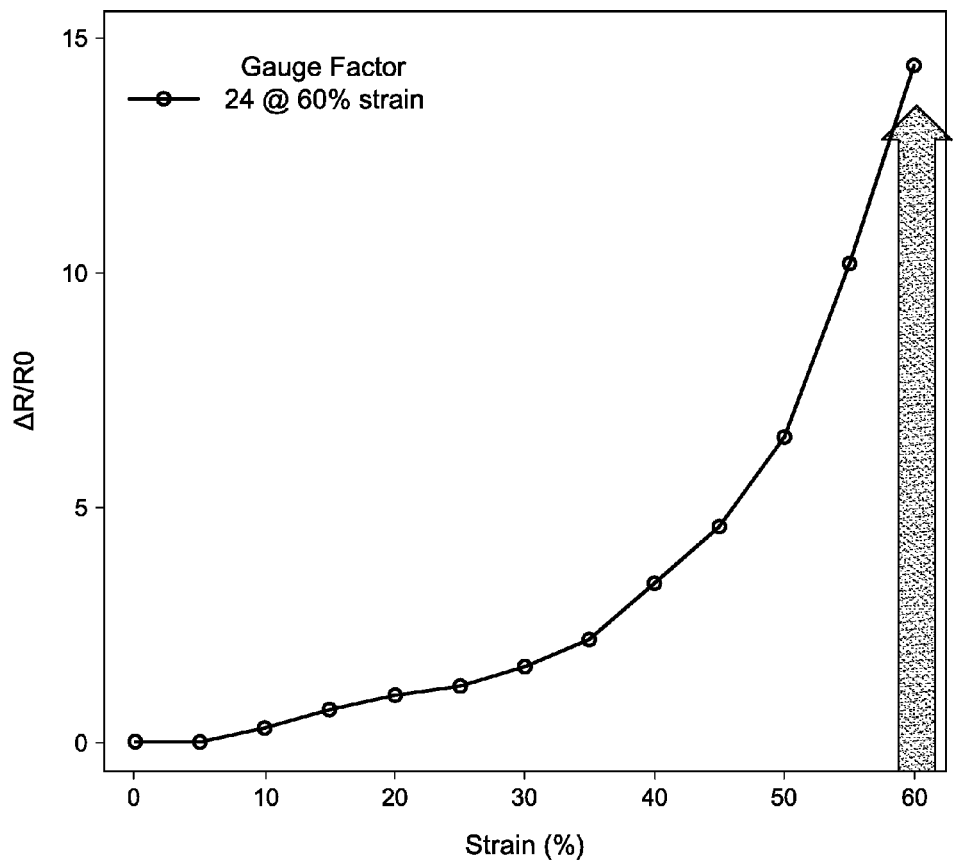
FIG. 8. (A) changes in resistance (ΔR/Ro) as a function of linear sensor stretch for sensor apparatus.
Figure 8B:
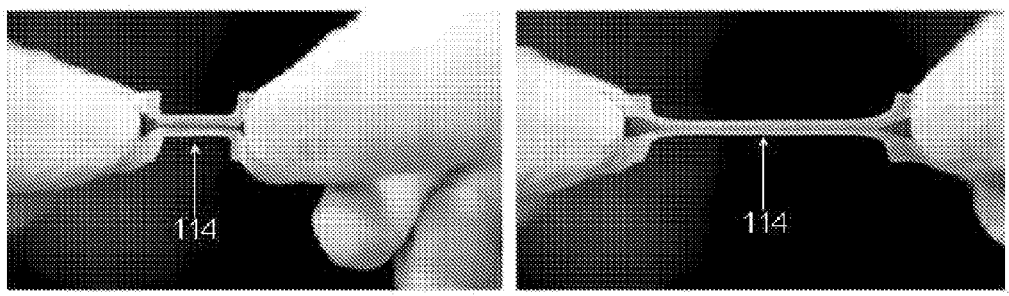
Figure 9B:
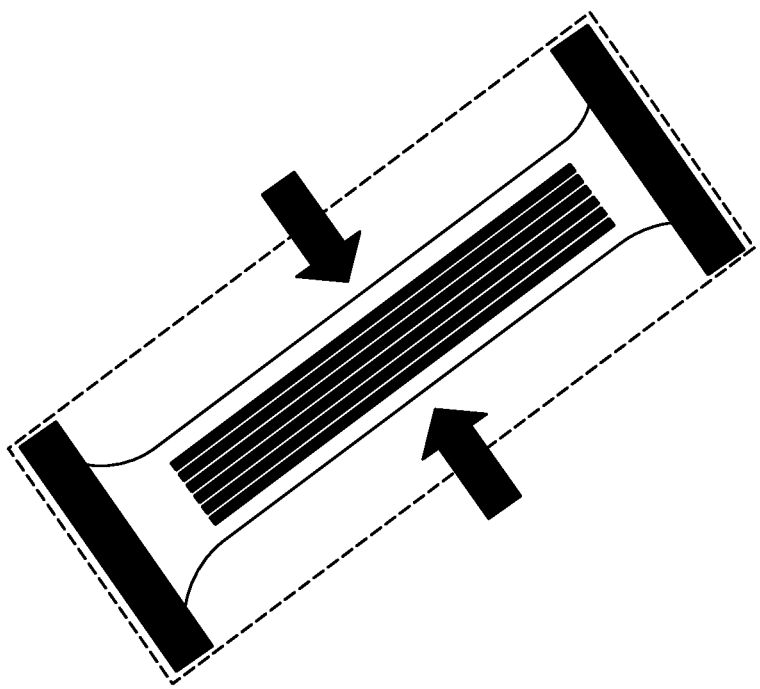
FIG. 9. Schematic of CNT densifying on polyolefin. (a) CNTs (1) on shape memory polymer, e.g., polyolefin (2), before shrinking. (b) CNTs on polyolefin after uniaxial shrinking (3) via heat resulting in densification.
Figure 9A:
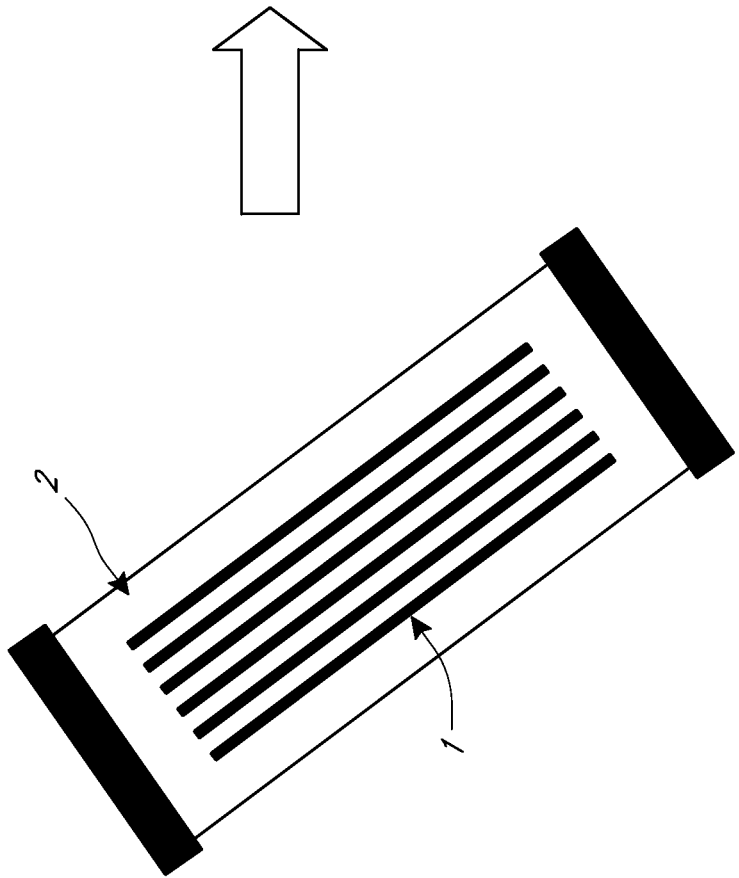

FIG. 7A shows another embodiment of a patient coupled portion 2' and FIG. 7B shows changes in resistance ($\Delta R/Ro$) as a function of strain sensed by a sensor apparatus 300. The patient coupled portion 2' includes a flexible interface 290. The flexible interface 290 includes a first end 292 and a second end 294 disposed on an end of the interface opposite the first end 292. The second end 294 is wider such that it can accommodate a sensor attachment module 320. The sensor attachment module 320 can be disposable or reusable.

The flexible interface 290 preferably includes an aperture 296 disposed along the length thereof between the first end 292 and the second end 294. The aperture 296 is configured to permit a sensor apparatus 300 to be inserted therethrough. When so inserted, the sensor apparatus 300 is located at or adjacent to the first end 292. The sensor apparatus 300 can be entirely disposed under and/or be covered by the expanse of the flexible interface 290. In one embodiment, signals are conveyed from the sensor apparatus 300 to the sensor attachment module 320 by a flex circuit 324 that is extends between the sensor apparatus 300 and the sensor attachment module 320. The flex circuit 324 can include a ribbon cable or assembly of a conductor disposed in a flexible, e.g., polymeric, sheet.

In one embodiment, the sensor apparatus 300, flex circuit 324 and sensor attachment module 320 are provided as an assembly. To apply the patient coupled portion 2', the patient threads the sensor apparatus 300 and the flex circuit 324 through the aperture 296 to dispose the sensor apparatus 300 beneath the flexible interface 290 in direct contact with the user's skin, e.g., directly on the skin of the abdomen just above the belly button. The flexible interface 290 can have an adhesive adapted for coupling with the skin at both the first end 292 and the second end 294. In one embodiment, the first end 292 has a central area in which the sensor apparatus 300 is disposed. The central area can be configured to minimize or reduce the tendency of the flexible interface 290 to create a source of error in the sensor output. For example, if the sensor is a strain gauge the central area can be configured to not have adhesive so that the sensor apparatus 300 can be trapped between the skin of the mother and the flexible interface 290 but not be rigidly adhered to the interface.

In one embodiment, the sensor attachment module 320 is disposable and can be shipped coupled with the flexible interface 290. After use, the sensor attachment module 320 and the flexible interface 290 can be disposed of. In another embodiment, the sensor attachment module 320 is reusable and is configured to be releasably coupled with the flexible interface 290. For example, the sensor attachment module 320 can be coupled and shipped with the flexible interface 290 but can be removed therefrom and reattached by the user to another the flexible interface 290. In one arrangement where the sensor attachment module 320 is reusable, the sensor apparatus 300 can be provided in an assembly with the flex circuit 324. In such arrangement, the flex circuit 324 and the sensor attachment module 320 preferably have connectors enabling the user to electrically couple the flex circuit 324 to the sensor attachment module 320.

Figure 10:
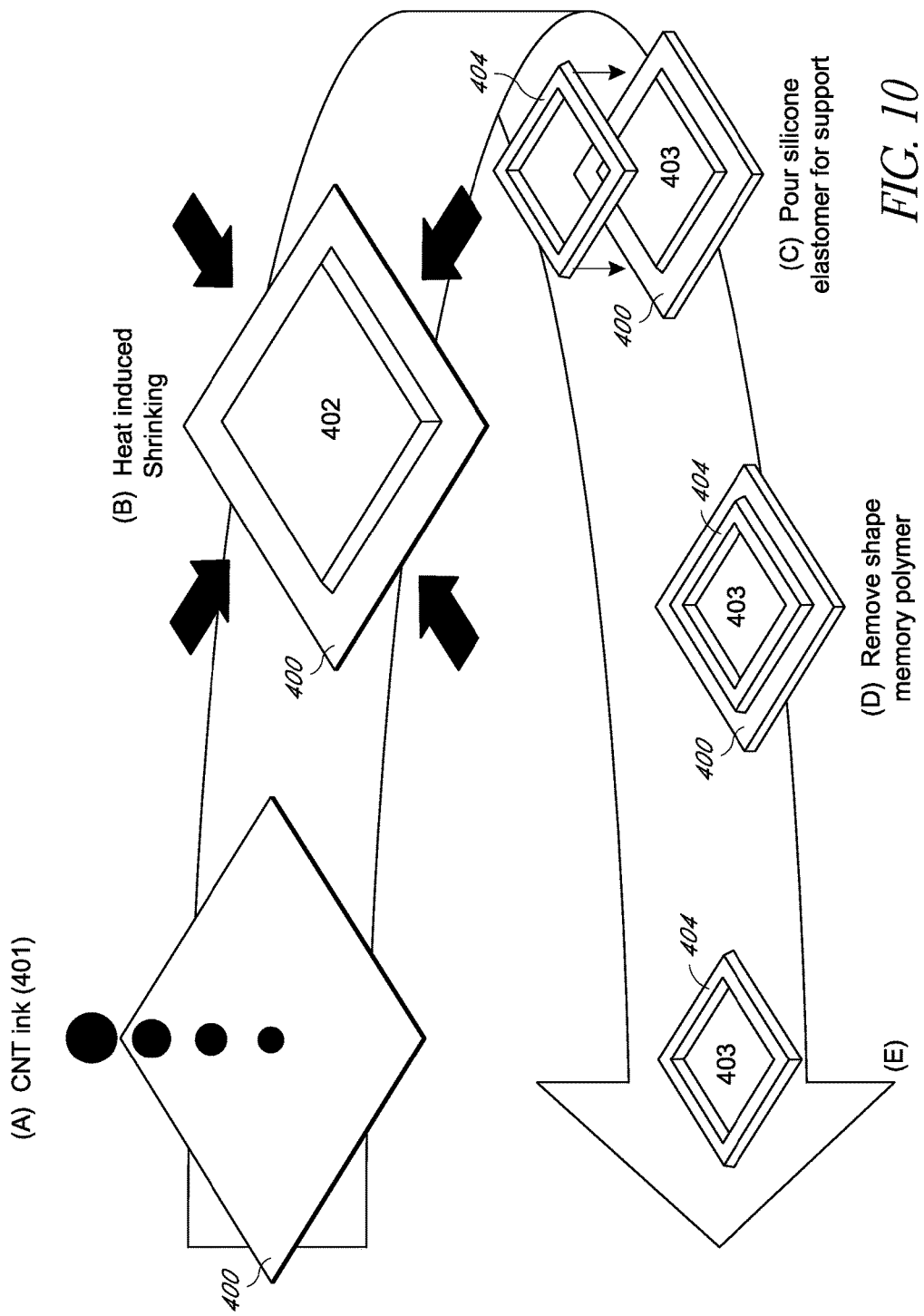
FIG. 10. Process flow for forming a wrinkled carbon nanotube (CNT) thin film. (A) Carbon nanotube ink is deposited on a flexible substrate; (B) Heat induced shrinking of preshrunk layer of CNT, resulting in shrunk CNT thin film; (C) Elastomer poured and cast onto shrunk CNT thin film; (D) Remove flexible substrate from shrunk CNT thin film and elastomer support; (E) shrunk CNT thin film with elastomer support.
Figure 11A:
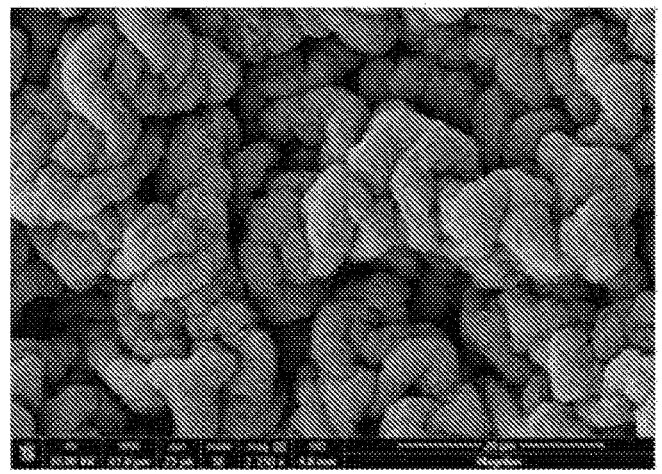
FIG. 11 (B) includes photographs of a sensor before and after linear stretch to 60% strain.
Figure 11B:
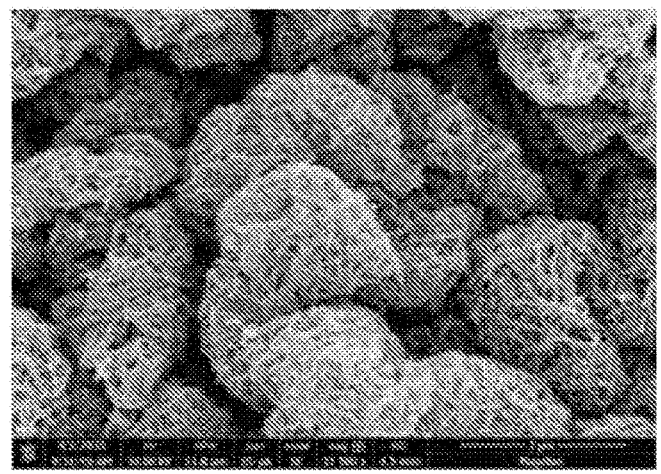
Figure 11C:
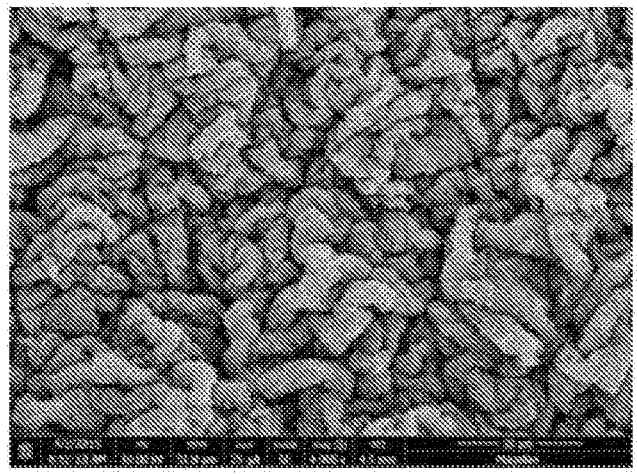
Figure 12B:
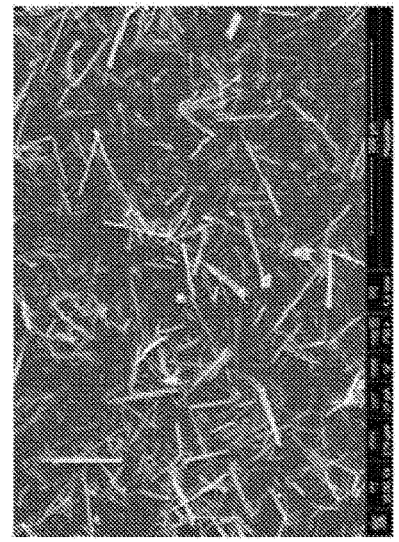
FIG. 12. SEM images of silicon nanowire films before and after shrinking. (A) Before shrinking, 102× magnification: (B) before shrinking, 750× magnification: (C) after shrinking, 103× magnification; (D) after shrinking, 750× magnification.
Figure 12D:
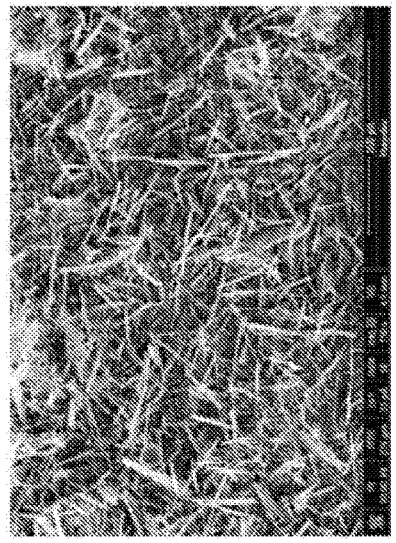
Figure 12A:
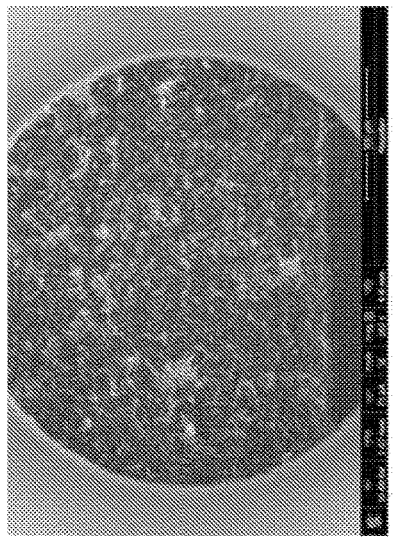
Figure 12C:
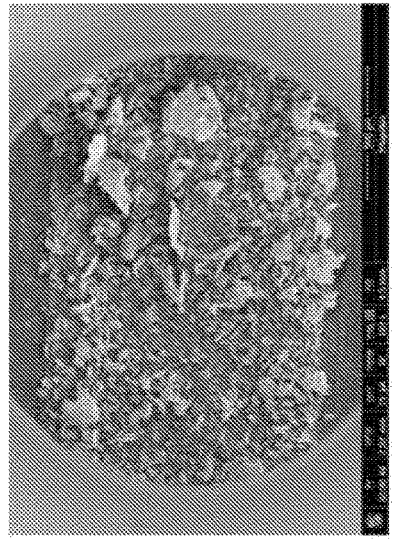

FIG. 10 shows a process flow for forming a wrinkled carbon nanotube (CNT) thin film. In panel A, carbon nanotube ink 401 is deposited on a flexible substrate 400. In panel B, heat induced shrinking of preshrunk layer of CNT 402 results in shrunk CNT thin film 403. In panel C, elastomer 404 is poured and cast onto shrunk CNT thin film 403. In panel D, flexible substrate 400 is removed from shrunk CNT thin film 403 and elastomer support 404. Panel E shows shrunk CNT thin film 403 with elastomer support 404.

2. Sensors Having a One Dimension Nanostructure

In some embodiments the sensor apparatus 100 includes one-dimensional (1D) nanostructures, such as those depicted in FIGS. 9-12. Such apparatus can include one or more of nanotubes, nanofibers, nanowires, and rods. A class of nanostructures includes nanoconductors. A nanostructure is said to be one dimensional, for example, if it much longer in one direction than in other directions perpendicular to the long direction, for example having a diameter on the order of a nanometer ($10^{-9}$ meters) and a length larger than 10 nm, larger than 50 nm, larger than 80 nm, larger than 90 nm or larger than 100 nm. Nanotubes include carbon nanotubes, for example. A nanowire is a nanostructure, with the diameter of the order of a nanometer ($10^{-9}$ meters). A nanostructure can be defined as the ratio of the length to width being greater than 1000. Many different types of nanowires exist, including superconducting (e.g., YBCO), metallic (e.g., Ni, Pt, Au), semiconducting (e.g., Si, InP, GaN, etc.), and insulating (e.g., $SiO_2$, $TiO_2$). As disclosed herein, a 1D nanostructure is densified and aligned to produce an effective conductor, which may be configured as a thin film.

Cost-effective technologies disclosed herein provide a process to highly densify and align 1D nanostructures, such as CNTs, to improve its conductivity using shrink technology. In some embodiments, this is done by depositing a thin film of CNTs on the surface of a shape memory polymer, such as polyolefin. Preferably the polymer is a chemically resistant shape memory polymer. The process includes uniaxially, biaxilally, or multiaxially shrinking the polymer by subjecting it to heat. Increasing the density and alignment of CNTs improves the conductivity of the assembly for strain gauge sensors and other applications that use CNTs. Other applications include batteries and chemical sensors.

We demonstrate that biaxial or multiaxially shrinkage of a CNT thin film produces wrinkled structures. As noted above, shrinking of metal films can produce wrinkling in the film. More generally, this wrinkling occurs if stiffness mismatch is provided between a substrate layer and a layer to be wrinkled or crumpled. We have found that a CNT thin film also produces wrinkling. It is believed that the total amount of van der Waals force between each individual CNTs is strong enough to create a stiff thin layer consequently wrinkling after biaxial or multiaxial shrinkage. This wrinkling phenomenon can be produced on shape memory polymers that shrink. We have also shown that the CNT thin film can be transferred onto a soft silicone substrate after removal of the shape memory polymer.

In some embodiments, the thin film of CNTs is shrunk by heating to a temperature of about 50° C., about 60° C., about 70° C., about 80° C., about 90° C. about 100° C., about 110° C., about 120° C., about 130° C., about 140° C., about 150° C., about 160° C. about 170° C., about 180° C., about 190° C., about 200° C., about 210° C., about 220° C., about 230° C., about 240° C., or about 250° C. or a range bounded by any two of the preceding numerical values.

A polyolefin is any of a class of polymers produced from a simple olefin (also called an alkene with the general formula $C_nH_{2n}$) as a monomer. For example, polyethylene is the polyolefin produced by polymerizing the olefin ethylene. An equivalent term is polyalkene.

In some embodiments, the CNTs are dispersed in a solution of an organic solvent, such as chloroform, prior to deposition on a shape memory polymer. Other non-limiting examples of organic solvents include benzene, toluene and phenyl ethyl alcohol or other solvents (Li et al. 2012 "Dispersion of Carbon Nanotubes in Organic Solvents Initiated by Hydrogen Bonding Interactions" AIChE Journal 58: 2997-3002; Dumonteil et al. 2006 "Dispersion of carbon nanotubes using organic solvents" J Nanosci Nanotechnol 6(5): 1315-1318; and Ausman et al. 2000 "Organic Solvent Dispersions of Single-Walled Carbon Nanotubes: Toward Solutions of Pristine Nanotubes" J Phys Chem B 104: 8911-8915).

Densifying CNTs in a sensor application increases the sensitivity of the sensor, proportional to the degree to which a shape memory polymer shrinks. For example, a 95% reduction in area by shrinking on a polyolefin enables a much higher responsiveness. In some embodiments, a stretch sensor or a strain gauge device, containing densified CNTs, has a correspondingly lower electrical resistance upon densification of the CNTs. In some embodiments, the resistance of a film upon densification is reduced to about 100 k$\Omega$. In some embodiments, the resistance of a film upon densification is reduced to about 10 k$\Omega$, about 50 k$\Omega$, about 100 k$\Omega$, about 150 k$\Omega$, about 200 k$\Omega$, about 250 k$\Omega$, about 300 k$\Omega$, about 350 k$\Omega$, about 400 k$\Omega$, about 450 k$\Omega$, about 500 k$\Omega$, about 550 k$\Omega$, about 600 k$\Omega$, about 650 k$\Omega$, about 700 k$\Omega$, about 750 k$\Omega$, about 800 k$\Omega$, about 850 k$\Omega$, about 900 k$\Omega$, about 950 k$\Omega$, about 1000 k$\Omega$, about 1100 k$\Omega$, about 1200 k$\Omega$, about 1300 k$\Omega$, about 1400 k$\Omega$ or about 1500 k$\Omega$ or a range bounded by any two of the preceding numerical values. A low resistance film allows the development of highly sensitive devices that were previously not feasible based on previously existing technologies.

In some embodiments, the density amplification of the CNTs relative to an initial density upon application of the CNTs to a shape memory polymer is an increase of about 100%, about 150%, about 200%, about 250%, about 300%, about 350%, about 400%, about 450%, about 500%, about 550%, about 600%, about 650%, about 700%, about 750%, about 800%, about 850%, about 900%, about 950%, about 1000%, about 1100%, about 1200%, about 1300%, about 14000% or about 1500% or a range bounded by any two of the preceding numerical values.

CNT density can be measured by a light transmittance test. In some embodiments, the CNT density results in light transmittance values of between about 30 to about 90%. In some embodiments the light transmittance is about 30%, about 35%, about 40%, about 45%, about 50%, about 55%, about 60%, about 65%, about 70%, about 75%, about 80%, about 85% or about 90% or a range bounded by any two of the preceding numerical values.

Examples Applications of Wrinkled CNT Structures
1. Flexible Devices

Wrinkled CNT thin films can be incorporated into flexible devices, such as in sensor apparatuses, including strain gauges. As noted above, the CNT thin films can form the sensing component of the sensor apparatus 100. An advantage of using wrinkled films in flexible devices is the ability to stretch out the wrinkles produced from shrinking. Depending on the shape memory polymer used, it is theoretically possible to stretch out to the original, pre-shrinkage dimensions.

Various applications benefit from strain gauges that can undergo large strains and still produce repeatable, predictable outputs. For example, it is desired that such a strain gauge or other sensor apparatuses can be mounted on a flexible substrate and connected to surfaces that are highly curved, mobile and/or repeatedly flexed during the duty cycle of the strain gauge or sensor apparatus. It would be useful for a sensor apparatus herein to be wearable to enable various health or physiological condition monitoring applications, such as for monitoring fetal or maternal health and more comprehensively progress of a pregnancy.

2. Piezoresistive and Capacitive Sensors with Wrinkled CNT Structures

Wrinkled CNT thin films can also be used in the fabrication of piezoresistive and capacitive sensors (Limpomi, D. J.; Vosgueritchian, M.; Tee, B. C-K.; Hellstrom, S. L.; Lee, J. A.; Fox, C. H.; Bao, Z. Nature Nanotech, 2011, 6, 788-792, incorporated herein by reference). As such CNT thin films can be used to provide a capacitive sensor for monitoring fetal or maternal health and more comprehensively progress of a pregnancy. Elastic conductors are advantageous components for use in electronic and optoelectronic devices that facilitate human interaction and biofeedback, such as interactive electronics, implantable medical devices and robotic systems with human-like sensing capabilities. The availability of conducting thin films with these properties provides a basis for the development of skin-like sensors that stretch reversibly, sense pressure, bend into hairpin turns, integrate with collapsible, stretchable and mechanically robust displays and solar cells, and also wrap around non-planar and biological surfaces such as skin and organs.

B. Examples

Example 1

Processing Guide for Transferring a Structured Metal Thin Film from a Shape-Memory Carrier onto a Silicon Elastomer This protocol is meant to serve as a processing guide for transferring wrinkled metal thin films from a substrate (e.g., Grafix Arts polystyrene shrink film) onto an elastomer (e.g., ECOFLEX30™ silicon elastomer). Specific parameters are given for platinum strain gauges and gold interconnects. Adjustments may be made for specific process applications.

Grafix Frisket Film is mounted to rigid PMMA support. A mask design is laser cut using Grafix Frisket Film using laser settings of 75% power and 100% speed. For convenience, scotch tape is placed across trace width before removing the mask from the support (in order to not distort trace width).

b. Polystyrene (PS) SMP (Grafix Arts)

Grafix PS sheets are laser cut with laser settings of 78% power, 100% speed and placed concave up (using weights to flatten edges) and then ligned length to length (orient such that long side is aligned with axis being stretched). The cut PS are washed with 70% EtOH and air dried. Alignment of the mask is made by peeling off the mask and setting on desk with adhesive side up. The PS sheet is taken up with concave side down and bend both edges so that the center will adhere first before smoothing it down along the sides c. Deposition Sputter deposition is used, setting Argon gas pressure to 4 psi using a vacuum pump. Check target and set target metal and run test: 2-5 nm terminal thickness. For strain gauges, use Platinum (10 nm). For interconnects, use Gold (15 nm).

2. Miniaturization

Bake using a toaster oven preheated to 160° C., shrinking samples 2-4 at a time. Let cool to room temperature before removing samples from baking tray 3. Anneal Preheat vacuum oven to 200° C. for ½-1 hour and bake for 15 min at 200° C. Place samples on copper plate and cool at room temp for 2 min. Repeat for 3× total. If curing ECOFLEX™ in same day, immediately set oven to 85° C. and open oven door)

4. Silane Treatment (Application of Adhesion Layer)

Prepare 5 mM of Mercaptorpopyl trimethoxy-silane in EtOH (e.g., 38 μm silane in 40 mL EtOH). Place samples in petri dish and pour silane solution over it (can do up to 6 samples at once per dish). Parafilm shut and leave for 1 hr at room temp. Rinse samples individually with EtOH wash bottle and air dry before preceding to transfer.

5. Transfer

For EF30 (ECOFLEX™) elastomer, mix components A:B at a 1:1 ratio. Degas: 5 min (pot Life: 45 min, cure time (rm temp): 4 hours). For spin coating, use program 4: Step 1: Ramp 300 rpm for 5 sec; Step 2:150 rpm 30 sec, acceleration is at 1200 rpm per min. For vacuuming and curing, vacuum for 20 min and cure in vacuum oven for 2 hours at 85° C. (can be left in overnight). For Etch ECOFLEX™ (EF), laser cut EF and place onto paper (use weights to flatten paper; Materials Database: Copier Paper). For laser cutting, use laser settings of 99.4% power, 100% speed. Use outline in paper to align sample. Scale as necessary as shrink process may cause variations in aspect ratio. For laser cut samples, use EF30. 1 mm, with laser settings of 100% power, 31% speed. For liftoff, use the following solvent baths: Acetone: 30 min at 55° C.; toluene: 10 min at 70° C. (gently agitate on hot plate in the last min or two). To dry, hang dry by corners using binder clips overnight.

Example 2

Densification and Alignment of CNTs Using Polyolefin

This was accomplished by first dispersing CNTs (0.05% wt/v) in a solution of chloroform. CNTs were sonicated for 30 minutes in an ice bath and centrifuged at 10,000 rpm for one hour. This process is also possible in aqueous solution. For example, CNTs can be dispersed into an aqueous solvent when a surfactant, such as sodium dodecyl sulfate (SDS), is present (Yu, J.; Grossiord, N.; Konin, C. E.; Loos, J. Carbon. 2007, 45(3), 618-623). The shape memory polymer was then heated to approximately 60° C. after which drop casting deposition was used to create a thin layer of CNTs. Drop casting is done by pipetting the CNT disperse solution on top of the heated shape memory polymer. The shape memory polymer was then left to dry in a closed container for two hours. In the case of using aqueous CNTs, after the shape memory polymer is dried, it is further washed with an aqueous solvent to remove any surfactants present on the shape memory polymer. The shape memory polymer is then left to dry in a closed container for two hours. After drying, the shape memory polymer was then clamped to a glass slide on two ends for uniaxial shrinking. The shape memory polymer was then shrunk in a conventional toaster oven at 150° C., which densified and aligned the CNTs on the surface of the shape memory polymer.

This process is extremely fast and efficient compared to other time consuming processes such as the Langmuir-Blodgett method. The process is very reproducible and does not require much dexterity. The density amplification of the CNTs is up to 770% due to the shrinking nature of polyolefin, which is more than two folds higher than previous shrinking technology. The process can also be done using almost any solvent suitable for obtaining a stable CNT dispersion.

Example 3

Biaxial or Multi-Axial Shrinkage of a CNT Thin Film to Produce a Wrinkled Structure One embodiment is a process to densify a CNT thin film to produce wrinkled structure using polyolefin, a chemically resistant shape memory polymer. This was accomplished by first dispersing CNTs (0.05% wt/v) in a solution of chloroform. CNTs were sonicated for 30 minutes in an ice bath and centrifuged at 10,000 rpm for one hour. This process is also possible in aqueous solution. For example, CNTs can be dispersed into an aqueous solvent when a surfactant, such as sodium dodecyl sulfate (SDS), is present (Yu, J.; Grossiord, N.; Konin, C. E.; Loos, J. Carbon. 2007, 45(3), 618-623). The shape memory polymer was then heated to approximately 60° C. after which drop casting deposition was used to create a thin layer of CNTs. Drop casting is done by pipetting the CNT disperse solution on top of the heated shape memory polymer. The shape memory polymer was then left to dry in a closed container for two hours. In the case of using aqueous CNTs, after the shape memory polymer is dried, it is further washed with an aqueous solvent to remove any surfactants present on the shape memory polymer. The shape memory polymer is then left to dry in a closed container for two hours. After drying, the shape memory polymer was permitted to undergo biaxial shrinking. The shape memory polymer was then shrunk in a conventional toaster oven at 150° C., resulting in a densified SiNW network on the surface of the shape memory polymer.

This process is extremely fast and efficient compared to other time consuming processes such as the Langmuir-Blodgett method. The process is very reproducible and does not require much dexterity. The density amplification of the CNTs is up to 770% due to the shrinking nature of polyolefin, which is more than two fold higher than previous shrinking technology. The process can also be done using almost any solvent suitable for obtaining a stable CNT dispersion.

Example 4

Deposition of a Confluent Film of Carbon Nanotubes onto the Surface of a Polyolefin In another process, a confluent film of carbon nanotubes is deposited onto the surface of a shape memory polymer, such as a polyolefin. In one embodiment, an airbrush is used to facilitate deposition of a confluent film of CNTs and greatly speed up the process.

Example 5

Biaxial or Multi-Axial Shrinking of a Silicon Nanowire (SiNW) Thin Film

SiNWs were synthesized by Si wafer using aqueous Ag-assisted electroless etching. A P-type, (1,0,0), 1-100 Ω/cm Si wafer was used to synthesize SiNWs in an aqueous solution of 0.02M AgNO3 and 5M HF acid. The lengths of the SiNWs can be controlled by the etching time. To remove the SiNWs from the Si wafer, the Si substrate was sonicated in isopropyl alcohol (IPA) for 30 seconds. The shape memory polymer was then heated to approximately 60° C. after which drop casting deposition was used to create a thin layer of SiNWs. Drop casting is done by pipetting the SiNW solution on top of the heated shape memory polymer. The shape memory polymer was then left to dry in a closed container for two hours. After drying, the shape memory polymer was permitted to undergo biaxial shrinking. The shape memory polymer was then shrunk in a conventional toaster oven at 150° C., resulting in a dense SiNW network on the surface of the shape memory polymer.

While the present description sets forth specific details of various embodiments, it will be appreciated that the description is illustrative only and should not be construed in any way as limiting. Furthermore, various applications of such embodiments and modifications thereto, which may occur to those who are skilled in the art, are also encompassed by the general concepts described herein. Each and every feature described herein, and each and every combination of two or more of such features, is included within the scope of the present invention provided that the features included in such a combination are not mutually inconsistent.

Some embodiments have been described in connection with the accompanying drawing. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Further, the actions of the disclosed processes and methods may be modified in any manner, including by reordering actions and/or inserting additional actions and/or deleting actions. Thus, it is intended that the scope of at least some of the present inventions herein disclosed should not be limited by the particular disclosed embodiments described above. The limitations in the claims are to be interpreted broadly based on the language employed in the claims and not limited to the examples described in the present specification or during the prosecution of the application, which examples are to be construed as non-exclusive.

What is claimed is:

1. A sensor apparatus comprising:
a flexible substrate comprising an elastomeric polymer, and
a wrinkled conductor comprising one or more of a metal film, a semiconductor structure, an array of one-dimensional structures and/or carbon black disposed on the flexible substrate,
wherein the flexible substrate is covalently bonded to the metal film, the semiconductor structure, the array of one-dimensional structures and/or the carbon black, and wherein conductor comprises secondary folding.

2. The sensor apparatus of claim 1, wherein the conductor is capable of repeatable variation in resistance when subject to a strain of up to about 300%.

3. The sensor apparatus of claim 1, wherein the secondary folding comprises micron-scaled invaginations in the surface of the conductor.

4. The sensor apparatus of claim 1, wherein the metal film comprises a gold layer.

5. The sensor apparatus of claim 1, wherein the metal film comprises a platinum layer.

6. The sensor apparatus of claim 1, wherein said elastomeric polymer is an elastomeric silicone film.

7. The sensor apparatus of claim 6, wherein said elastomeric silicone film comprises polydimethylsiloxane.

8. A sensor apparatus comprising:
a flexible substrate comprising an elastomeric silicon film, and
a wrinkled conductor disposed on the flexible substrate, wherein said conductor comprises gold and wherein said elastomeric silicone film is covalently bonded to the gold by (3-mercaptopropyl) trimethoxysilane (MPTMS), as a self-assembled monolayer.

9. The sensor apparatus of claim 8, wherein said conductor further comprises platinum and wherein said platinum is bonded to said gold by metallic bonds.

10. The sensor apparatus of claim 1, wherein the one-dimensional structure is selected from the group consisting of a nanotube, a nanofiber, a nanowire and a rod.

11. The sensor apparatus of claim 10, wherein the nanotube is a carbon nanotube (CNT).

12. The sensor apparatus of claim 10, wherein the nanowire is a silicon nanowire.

13. The sensor apparatus of claim 1, wherein the array of one-dimensional structures has a light transmittance value of about 40%.

14. A gauge, device comprising: a strain gauge, wherein the strain gauge comprises:
a flexible substrate, and
a conductor deposited on the flexible substrate, wherein the conductor comprises micron-scale invaginations.

15. The strain gauge of claim 14, wherein the micron-scale invaginations comprise a heterogeneous topographical portion.

16. The strain gauge of claim 14, wherein the flexible substrate is configured to be mounted to the skin of a user or patient.

17. A method of sensing a health condition of a user or patient, comprising:
coupling a sensor apparatus to a surface of a user or patient overlying structures to be monitored, wherein the sensor apparatus comprises a flexible substrate and a wrinkled conductor disposed on the flexible substrate, the wrinkled conductor being capable of detecting strain;
directing current through the sensor apparatus during flexing of the surface; and
measuring a characteristic of the sensor apparatus based on the strain to generate an output for a user indicative of the condition of the structures to be monitored.

18. The method of claim 17, wherein the characteristic of the sensor is a change in the resistance of a conductor thereof.

19. The method of claim 17, wherein movement of the surface is in response to breathing of the patient or user and the output indicates respiration of the user or patient.

20. The method of claim 17, wherein movement of the surface is in response to motion of the underlying structure.

* * * * *